United States Patent
Novak

(10) Patent No.: US 9,775,968 B2
(45) Date of Patent: Oct. 3, 2017

(54) MAGNETICALLY CONTROLLED STIFFNESS OF MATERIALS

(71) Applicant: Abbott Medical Optics Inc., Santa Ana, CA (US)

(72) Inventor: Curt A Novak, Corona, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 338 days.

(21) Appl. No.: 13/841,471

(22) Filed: Mar. 15, 2013

(65) Prior Publication Data

US 2014/0276899 A1    Sep. 18, 2014

(51) Int. Cl.
| | |
|---|---|
| A61M 25/01 | (2006.01) |
| A61F 9/007 | (2006.01) |
| A61M 25/00 | (2006.01) |
| A61M 5/00 | (2006.01) |
| F16K 7/02 | (2006.01) |
| F16K 13/10 | (2006.01) |
| A61L 29/12 | (2006.01) |
| A61B 17/00 | (2006.01) |

(52) U.S. Cl.
CPC ..... *A61M 25/0158* (2013.01); *A61F 9/00736* (2013.01); *A61L 29/126* (2013.01); *A61M 5/007* (2013.01); *A61M 25/0043* (2013.01); *F16K 7/02* (2013.01); *F16K 13/10* (2013.01); *A61B 2017/00876* (2013.01); *A61M 25/0074* (2013.01); *A61M 25/0127* (2013.01); *A61M 2025/0063* (2013.01)

(58) Field of Classification Search
CPC .......... A61M 25/1036; A61M 25/0009; A61M 25/0054; A61M 25/0127; A61M 25/0158; A61M 25/0043; A61M 2025/0059; A61M 2025/0063; A61B 2017/00876
USPC .......................................... 604/525
See application file for complete search history.

(56) References Cited

U.S. PATENT DOCUMENTS

| | | | |
|---|---|---|---|
| 2006/0051535 A1* | 3/2006 | Arney ............... | A61M 25/0009 428/34.1 |
| 2006/0079832 A1* | 4/2006 | Akahoshi ............ | A61M 1/0084 604/43 |
| 2006/0192465 A1* | 8/2006 | Kornbluh .................. | B64C 3/48 310/309 |
| 2008/0097399 A1* | 4/2008 | Sachar .............. | A61M 25/0054 604/525 |
| 2009/0012610 A1 | 1/2009 | Olson et al. | |

(Continued)

FOREIGN PATENT DOCUMENTS

| | | |
|---|---|---|
| DE | 102008057575 A1 | 5/2010 |
| EP | 2015376 A1 | 1/2009 |

OTHER PUBLICATIONS

Bossig G., et al., "Electroactive and Electrostructured Elastomers." International Journal of Modern Physics B. 2001, vol. 15 (6 & 7), pp. 564-573.

(Continued)

*Primary Examiner* — Kevin C Sirmons
*Assistant Examiner* — Amber Stiles
(74) *Attorney, Agent, or Firm* — Abbott Medical Optics Inc.

(57) ABSTRACT

A system and method for the use of magneto-rheological fluids (MRF) and magnetically controlled elastomers (MCE) for use in fluid control and distribution apparatus which are responsive to control by a magnetic field are disclosed.

12 Claims, 2 Drawing Sheets

(56) References Cited

U.S. PATENT DOCUMENTS

2010/0305477 A1    12/2010    Von Weymarn-Scharli
2011/0190683 A1*    8/2011    Gellman ........... A61M 25/0054
                                                                604/6.16
2012/0123328 A1*    5/2012    Williams .......... A61M 25/0043
                                                                604/95.05

OTHER PUBLICATIONS

Bustamante R., et al., "On a New Class of Electroelastic Bodies. I," Proceedings of the Royal Society A, 2013, 469, published Nov. 14, 2012.

International Search Report and Written Opinion for Application No. PCT/US2014/018534 mailed on Apr. 24, 2014, 17 pages.

Ruddy C., et al., A Review of Magnetorheological Elastomers: Properties and Applications, Advances Manufacturing Science Research Center, Mechanical Engineering, University College Dublin, Belfield, Dublin 4, Ireland.

Varga Z., et al., "Magnetic Feld Sensitive Functional Elastomers with Tuneable Elastic Modulus," Polymer, 2006, vol. 47, pp. 227-233.

* cited by examiner

MAGNETICALLY CONTROLLED STIFFNESS OF MATERIALS

FIELD OF THE INVENTION

The instant disclosure relates to the use of magneto-rheological fluids (MRF) and magnetically controlled elastomers (MCE) for use in fluid control and distribution apparatus which are responsive to control by a magnetic field.

BACKGROUND

Materials whose rheological properties may be varied by application of magnetic fields belong to a specific class of so-called smart materials because they can respond, via solid-state electronics and modern control algorithms, to changes in their environment. Such electroactive elastomers are composites made of solid particles embedded in an elastomeric network whose mechanical or optical properties can be changed by the application of an electric or a magnetic field.

An applied current or field aligns the particles and provides a structure to the doped materials. More specifically, magneto-rheological fluids (MRF) and magnetically controlled elastomers (MCE) are compounds that respond to a magnetic field. The response exhibited is immediate and reversible with a change in rheological behavior, for (MRFs) or elastic behavior, for MCEs. In both cases, ferromagnetic particles, such as iron, are suspended in a carrier liquid. The carrier liquid in MRFs may be mineral oil and may be a rubber matrix in an MCE. In each, the iron particles may be present in sizes ranging from 3-10 micron in diameter. Additional types of filled elastomers include those based on carbonyl iron particles and silica particles, for example.

SUMMARY

It is to be understood that both the foregoing general description and the following detailed description are exemplary and explanatory and are intended to provide further explanation of the invention as claimed.

The present invention provides a phacoemulsification flow rate control system, comprising at least one tube comprising an MCE seeded portion, and at least one magnetic field source communicatively coupled to the MCE seeded portion wherein the at least one tube exhibits increased rigidity in response to the activation of the at least one magnetic field.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical optical and surgical devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Figure 1:
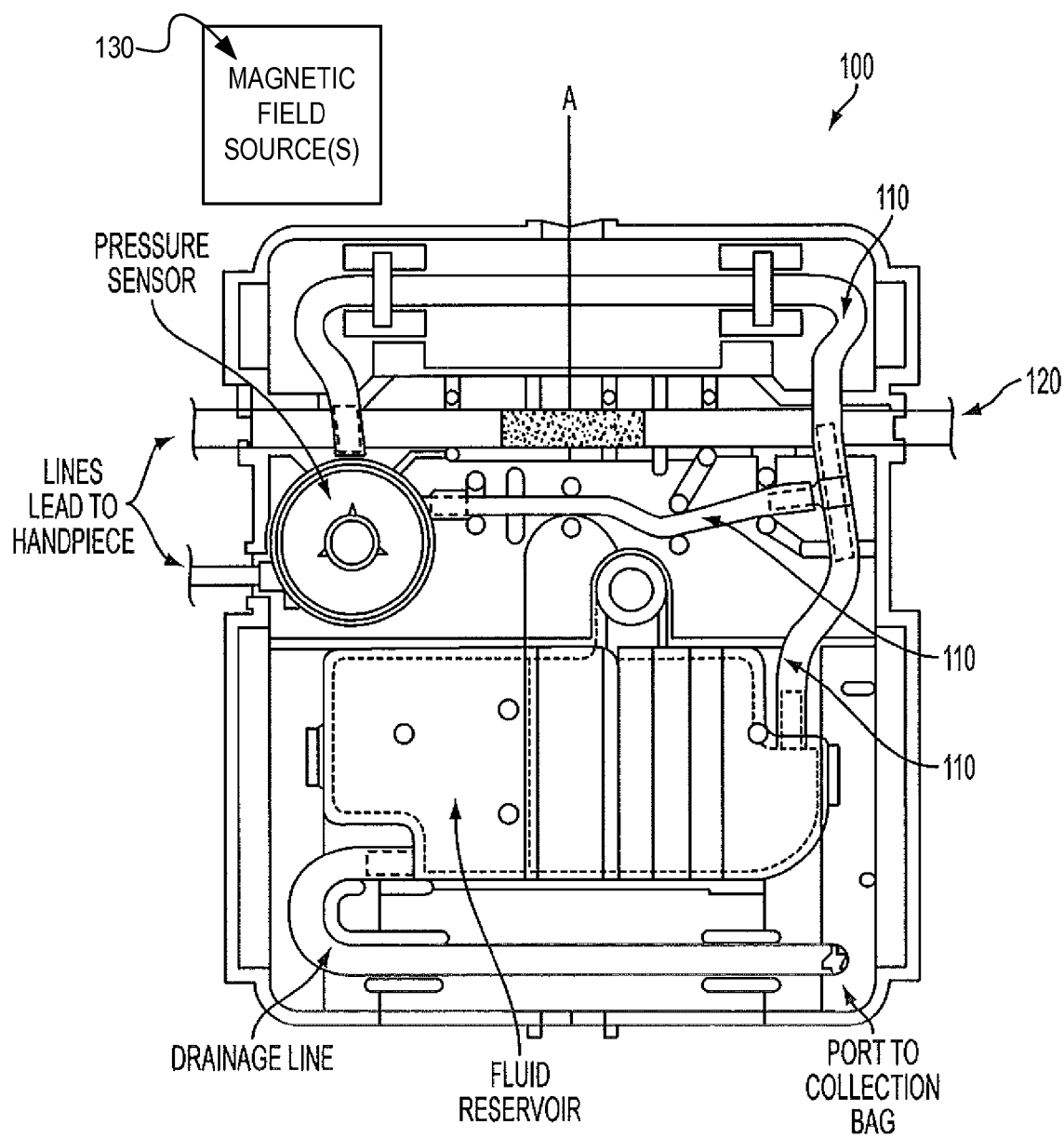
FIG. 1 illustrates an embodiment of the present invention.

Fluid sensing, control in feedback is hindered by low durometer (low modulus, low hardness) tubing which carriers aspiration and irrigation fluid between phaco console and handpiece tip. In an embodiment of the present invention, a tubing pack my utilize nylon and silicon tubing, for example, constructed with at least one MCE. As illustrated in FIG. 1, a tubing subcomponent 110 of a cassette 100 may be seeded with a suspension of ferromagnetic iron or ferrite particles during the extrusion process. When in use, the subcomponent 110 may be controlled using a magnetic field to control and/or expand the particle lattice of the subcomponent 110.

For example, an irrigation line 120, which may or may not form an aspect of the cassette 100, may have at least one line portion seeded for use as an MCE. By way of example, portion A of irrigation line 120 may be seeded and may be effected by a magnetic field produced from a source 130 located on the console (not shown) in which the cassette may be placed. The activation of the MCE properties of portion A may be used to restrict flow within the irrigation line.

The present invention may also be used with fluid packs and other fluid sources for which delivery and/or receive product material through a tube. For example, an MCE seeded silicon section of tubing may be between a pressure sensor and a vacuum pump in a phacoemulsification assembly. When phacoemulsification is activated, an electromagnetic field may be simultaneously activated in proximity to the MCE seeded section of tubing which may allow the tubing to become rigid and maintain a constant volume within its passageway. Thus, flow rate and pressure changes imparted one side of the MCE seeded portion may be instantaneously and substantially reflected on the other side of the MCE seeded portion.

For example, an MCE seeded section of tubing may be between a phaco handpiece and fluid reservoir, e.g. of a vacuum based pump (e.g. Venturi pump)) in a phacoemulsification system. When aspiration vacuum or pumping is activated at the console, an electromagnetic field may be activated (simultaneously or soon after activation) in proximity to the MCE seeded section of tubing which may allow the tubing to become rigid and maintain a constant volume within the passageway. Thus, flow rate and pressure changes imparted at the handpiece tip may be instantaneously or simultaneously, and substantially reflected at the vacuum pump. Similarly, flow rate and/or pressure changes imparted at the vacuum pump may be instantaneously or simultaneously, and substantially reflected at the handpiece tip. Thus, fluid communication between the handpiece tip and pump is improved. In addition, this also improved followability at the handpiece tip and/or reduces any lag time between activation of the pump and actual removal of fluid/debris from the surgical site.

In an embodiment of the present invention, a tubing section may also use MCE seeding to control a pumping action without physical contact with a mechanical force as would be imparted by, for example, a roller pump, by exposing the seeded portion to a pulsing and/or cycling electromagnetic field. The use of such a dynamic magnetic field may cause the seeded portion to expand and contract and create a positive displacement pumping motion. Similarly, MCE doped silicon material may be used as a pump bladder or reservoir, such as that illustrated in FIG. 1, and may provide both a pumping and storage source/mechanism in one combined structure of various shapes.

In an embodiment of the present invention, a catheter may be constructed with at least one MCE and may be placed in-vitro and have its stiffness characteristics changed when exposed to a magnetic flux. The MCE may include ferromagnetic iron particles in the about 3 to about 10 micron range and may be suspended in an elastic matrix carrier such as, for example, PBX, pellethane, nylon, polyethylene and/or polyurethane. By way of further example, nano-sized ferrite may be suitable for use with the present invention and may be preferably used with in a range of about 100 to about 300 nm. Such a material is also known as an Elastomer-Ferromagnet Composite (EFC). The addition of a magnetic field to the materials described above will increase the material sheer stress, resulting in increased stiffness.

As illustrated in FIG. 2, a catheter subcomponent such as inner, outer lumens and balloon may be seeded with a suspension of ferromagnetic iron or ferrile particles. During the extrusion process following extrusion, the composite may be placed in a controlled magnetic field so that ferromagnetic particles lattice may be held in place. Upon completion of the catheter process, the magnetic field is removed and the lattice relaxed.

Figure 2A:
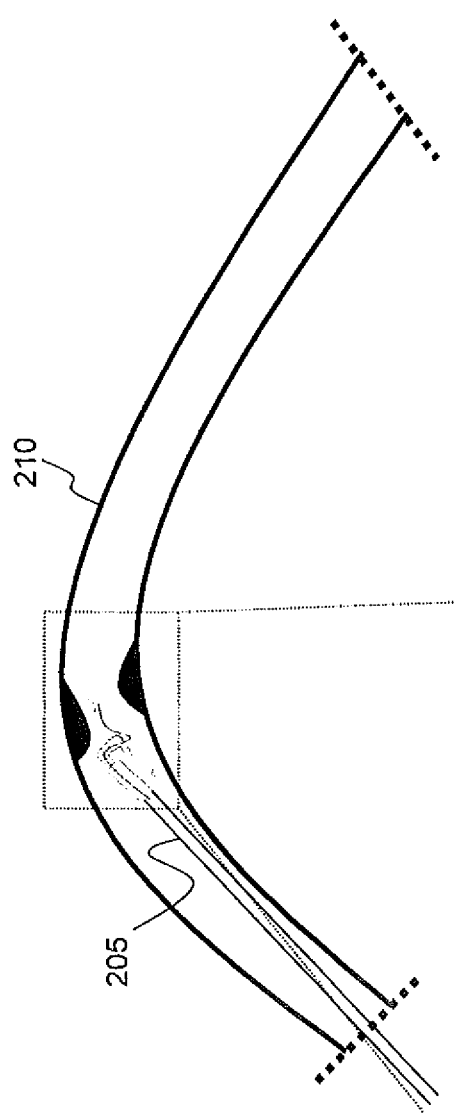
FIGS. 2a-2c illustrate embodiments of the present invention.

As illustrated in FIG. 2a, a catheter 205 may comprise a balloon 240 and a ferromagnetic seeded composite tip 250, may be placed within a vein 210. As illustrated in FIG. 2b, the push of the catheter 205 through vein 210 may be impeded by at least one object or restriction 230 which may comprise, for example, plaque deposits. More particularly, a guide wire 220 may become "stuck" or may not allow the catheter 205 to be advanced a smoothly as desired where forcing the catheter 205 and/or guide wire 220 might cause a rupture in the vein 210.

Figure 2C:
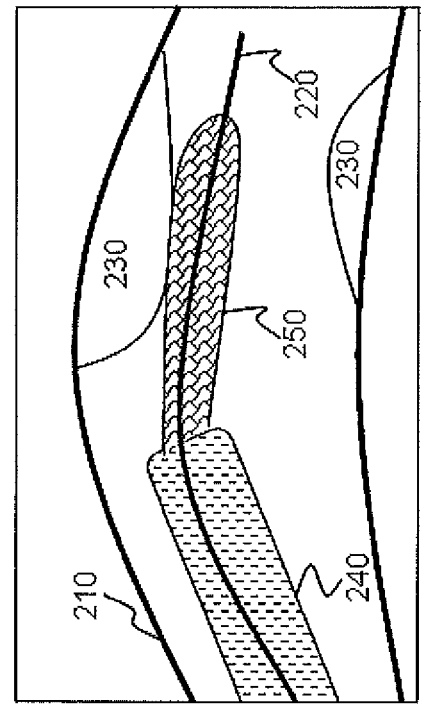
Figure 2B:
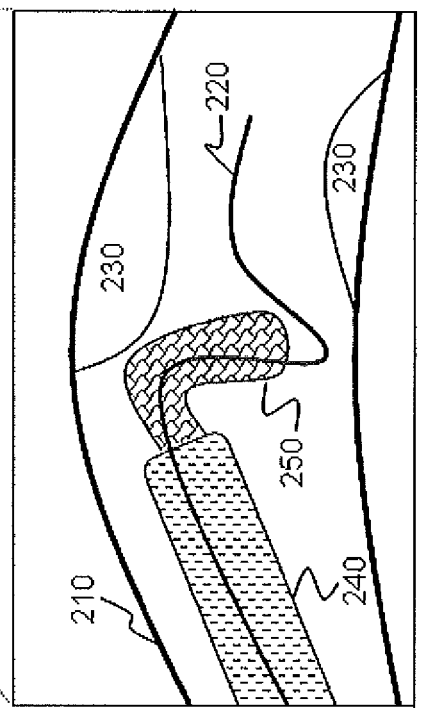

As illustrated in FIG. 2c, to overcome any foreign objects 230, for example, an electromagnetic field may be placed over the subject with implant in proximity to the catheter 205 to sufficiently align the particles in the seeded composite tip 250 so as to allow the seeded composite tip 250 to become substantially rigid. In this way, the guide wire 220 and/or the catheter 205 may have improved maneuverability around objects or restrictions 230. During the removal process, seeded composite tip 250 may be relaxed with the removal of the electromagnetic field.

In addition to the use with a catheter, the present invention may be used with any dilatation catheter, stent delivery catheter, or guidewire product where variable rheological material characteristics are needed.

Although the disclosure has described and illustrated exemplary embodiments with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A flow rate control system, comprising:
a tube connected between a handpiece and a fluid reservoir and comprising a magnetically controlled elastomers (MCE) seeded portion; and
a magnetic field source communicatively coupled to the MCE seeded portion;
wherein the tube is configured to exhibit increased rigidity in response to activation of the magnetic field source when the tube is positioned for use,
wherein the MCE seeded portion includes magnetic particles suspended in a carrier liquid, and
wherein the tube is configured to expand and contract in response to activation and deactivation of the magnetic field source.

2. The flow rate control system of claim 1, wherein the system is configured for a phacoemulsification system.

3. The flow rate control system of claim 1, wherein the tube is part of an aspiration system.

4. The flow rate control system of claim 1, wherein the tube is part of an irrigation system.

5. The flow rate control system of claim 1, further comprising a second tube comprising a second magnetically controlled elastomers (MCE) seeded portion and a second magnetic field source communicatively coupled to the second MCE seeded portion.

6. The flow rate control system of claim 5, wherein the tube is part of an aspiration system and the second tube is part of an irrigation system.

7. The flow rate control system of claim 6, wherein the system is configured for a phacoemulsification system.

8. The flow rate control system of claim 1, further comprising an aspiration pump, wherein the aspiration pump is coupled with the tube.

9. The flow rate control system of claim 8, wherein the aspiration pump is a vacuum based pump.

10. The flow rate control system of claim 1, wherein the tube is configured such that the increased rigidity is reversible in response to the magnetic field source being deactivated.

11. The flow rate control system of claim 1, wherein the magnetic field source is configured to produce a cycling electromagnetic field and the tube is configured to expand and contract in response to the cycling magnetic field to produce a pumping action.

12. The flow rate control system of claim 1, wherein the tube is a component of a cassette.

* * * * *